(12) United States Patent
Kim et al.

(10) Patent No.: US 11,389,067 B1
(45) Date of Patent: Jul. 19, 2022

(54) METHOD AND DEVICE FOR SCANNING BLOOD VESSELS

(71) Applicant: DOTTER INC., Incheon (KR)

(72) Inventors: Hungil Kim, Incheon (KR); Sogi Choi, Incheon (KR); Jongwoo Han, Incheon (KR); Jiyoon Lee, Incheon (KR)

(73) Assignee: DOTTER INC., Incheon (KR)

( * ) Notice: Subject to any disclaimer, the term of this patent is extended or adjusted under 35 U.S.C. 154(b) by 0 days.

(21) Appl. No.: 17/620,450

(22) PCT Filed: Jun. 4, 2020

(86) PCT No.: PCT/KR2020/007244
§ 371 (c)(1),
(2) Date: Dec. 17, 2021

(87) PCT Pub. No.: WO2021/085782
PCT Pub. Date: May 6, 2021

(30) Foreign Application Priority Data

Oct. 28, 2019 (KR) .................. 10-2019-0134617

(51) Int. Cl.
*A61B 1/00* (2006.01)
*A61B 5/00* (2006.01)
*A61M 25/00* (2006.01)
*A61M 25/10* (2013.01)

(52) U.S. Cl.
CPC .......... *A61B 5/0071* (2013.01); *A61B 5/0066* (2013.01); *A61B 5/6852* (2013.01); *A61B 5/6853* (2013.01); *A61M 25/0043* (2013.01); *A61M 25/10* (2013.01); *A61M 2025/0057* (2013.01); *A61M 2025/1052* (2013.01); *A61M 2205/0238* (2013.01)

(58) Field of Classification Search
CPC ....... A61B 5/0066; A61B 5/0071; A61B 1/00; A61B 5/00; A61B 18/22
See application file for complete search history.

(56) References Cited

U.S. PATENT DOCUMENTS

2006/0058622 A1    3/2006   Tearney et al.

FOREIGN PATENT DOCUMENTS

| EP | 3841965 A1 | 6/2021 |
|----|------------|--------|
| JP | 2016127993 A | 7/2016 |
| JP | 2017513645 A | 6/2017 |
| KR | 1020070058523 A | 6/2007 |
| KR | 101400288 B1 | 5/2014 |
| KR | 1020160027441 A | 3/2016 |
| KR | 101784363 B1 | 10/2017 |
| KR | 1020180106606 A | 10/2018 |
| KR | 1020190045569 A | 5/2019 |
| KR | 102095794 B1 | 4/2020 |

*Primary Examiner* — Deanna K Hall
(74) *Attorney, Agent, or Firm* — Umberg Zipser LLP; Ryan Dean

(57) ABSTRACT

Disclosed is a method of scanning a blood vessel according to several exemplary embodiments of the present disclosure. The method may include: inserting a first catheter for applying a fluorescent material into the blood vessel; applying the fluorescent material to a target point in the blood vessel using the first catheter; inserting a second catheter for scanning the blood vessel into the blood vessel after removing the first catheter from the blood vessel; and acquiring microstructure information and biochemical information of the blood vessel by using the second catheter after the second catheter is inserted into the blood vessel.

12 Claims, 8 Drawing Sheets

METHOD AND DEVICE FOR SCANNING BLOOD VESSELS

TECHNICAL FIELD

The present disclosure relates to a method and an apparatus for scanning a blood vessel, and more particularly, to a method and an apparatus for scanning a blood vessel that acquire microstructure information and biochemical information of a blood vessel.

BACKGROUND ART

As technologies of vascular imaging catheters used to diagnose cardiovascular diseases in the related art, intravascular ultrasonography, intravascular near-infrared imaging, and intravascular optical coherence tomography are commercially available and used in clinical practice.

The intravascular ultrasonography is a technology for acquiring tomography images of a blood vessel by inserting a device in the form of a catheter into the blood vessel, and the intravascular ultrasonography is most widely used as an intravascular imaging technology in hospitals. Because the intravascular ultrasonography uses ultrasound, the resolution is as low as about 100 μm, the contrast is also low, and the image acquisition speed is as low as about 30 seconds.

The intravascular near-infrared imaging is a commercially available technology that detects the presence of lipid in an inner wall of a blood vessel by a spectroscopic method using near-infrared rays. Recently, the intravascular near-infrared imaging is being developed using a single catheter combined with intravascular ultrasonography.

Because the near-infrared imaging uses light, there is a problem in that the sensitivity of signals is not constant depending on the presence or absence of blood in the blood vessel, the resolution is low, and the image acquisition speed is also low because the intravascular ultrasonography is also performed.

Meanwhile, the intravascular optical coherence tomography refers to a technology for acquiring tomography images of the blood vessel by inserting a device in the form of a catheter into the blood vessel, like the intravascular ultrasonography, providing light to the blood vessel, and analyzing reflected light.

The intravascular optical coherence tomography, which was initially developed, had a low speed at an intravascular ultrasonic level, and thus could not be widely used. However, second-generation intravascular optical coherence tomography, which has been developed recently, has a speed improved by 10 times or higher and thus may capture images in the blood vessel within several seconds.

Since the intravascular optical coherence tomography also uses light, this technology acquires images by performing flushing with a solution made by mixing a saline solution and a vascular contrast agent in order to minimize an influence of the blood. The intravascular optical coherence tomography has the resolution (~10 pin) improved by about 10 times in comparison with the intravascular ultrasonography, and as a result, the intravascular optical coherence tomography may advantageously detect a minute change in the blood vessel.

Meanwhile, recently, a multifunctional imaging technology is being developed at a laboratory level, in which the technologies in the related art are combined or a fluorescence imaging technology is further added to the technologies in the related art in order to more accurately diagnose an abnormality of the blood vessel.

Document of Related Art: Korean Patent Application Laid-Open No. 10-2016-0027441

SUMMARY OF THE INVENTION

The present disclosure has been made in consideration of the background art, and an object of the present disclosure is to provide a method and an apparatus for scanning a blood vessel.

Technical problems of the present disclosure are not limited to the aforementioned technical problems, and other technical problems, which are not mentioned above, may be clearly understood by those skilled in the art from the following descriptions.

In order to achieve the above-mentioned object, several exemplary embodiments of the present disclosure provide a method of scanning a blood vessel. The method may include: inserting a first catheter for applying a fluorescent material into the blood vessel; applying the fluorescent material to a target point in the blood vessel using the first catheter; inserting a second catheter for scanning the blood vessel into the blood vessel after removing the first catheter from the blood vessel; and acquiring microstructure information and biochemical information of the blood vessel by using the second catheter after the second catheter is inserted into the blood vessel.

The first catheter may have an expandable balloon coated with the fluorescent material at a distal end.

The applying of the fluorescent material to the target point in the blood vessel using the first catheter may include expanding the expandable balloon of the first catheter so that the expandable balloon contacts an inner wall of the blood vessel at the target point and the fluorescent material is applied to the inner wall of the blood vessel at the target point.

The first catheter may include: a balloon; a fluid transfer tube having the balloon at a distal end and transferring a fluid to the balloon so that the balloon is expandable; and a fluorescent material transfer tube having at least one micro-hole in a first region in a horizontal direction and transferring the fluorescent material to the at least one micro-hole so that the fluorescent material is discharged from the at least one micro-hole.

The applying of the fluorescent material to the target point in the blood vessel using the first catheter may include: expanding the balloon to block a region of the blood vessel corresponding to the target point in the blood vessel; and discharging the fluorescent material to an outside of the fluorescent material transfer tube through the at least one micro hole when the balloon is expanded.

The acquiring of the microstructure information and the biochemical information of the blood vessel by using the second catheter after the second catheter is inserted into the blood vessel may include acquiring an optical coherence tomography image together with a near-infrared fluorescence image of the target point using the second catheter.

In order to achieve the above-mentioned object, several exemplary embodiments of the present disclosure provide an apparatus for scanning a blood vessel. The apparatus may include: a first catheter for applying a fluorescent material to a target point in the blood vessel; a second catheter for scanning the target point in the blood vessel to which the fluorescent material is applied; a driving unit for rotating and moving the first catheter or the second catheter; and a data analysis unit that acquires microstructure information and biochemical information of the blood vessel based on scanning data scanned by the second catheter.

The first catheter may have an expandable balloon coated with the fluorescent material at a distal end.

The apparatus may further include a pressure control unit coupled to a proximal end of the first catheter and injecting a fluid for expanding the expandable balloon into the expandable balloon so that the expandable balloon contacts an inner wall of the blood vessel at the target point so that the fluorescent material is applied to the inner wall of the blood vessel at the target point.

The first catheter may include: a balloon; a fluid transfer tube having the balloon at a distal end and transferring a fluid to the balloon so that the balloon is expandable; and a fluorescent material transfer tube having at least one micro-hole in a first region in a horizontal direction and transferring the fluorescent material to the at least one micro-hole so that the fluorescent material is discharged from the at least one micro-hole.

The apparatus may further include: a pressure control unit coupled to a proximal end of the first catheter and injecting a fluid for expanding the balloon into the balloon for blocking a region of the blood vessel corresponding to the target point in the blood vessel; and a fluorescent material injection port provided at a proximal portion of the fluorescent material transfer tube and into which the fluorescent material is injected.

The microstructure information may include optical coherence tomography images, and the biochemical information may include near-infrared fluorescence images.

The technical solutions obtained by the present disclosure are not limited to the aforementioned technical solutions, and other technical solutions, which are not mentioned above, will be clearly understood by those skilled in the art from the following description.

The present disclosure may provide the method and the apparatus for scanning a blood vessel, which are capable of shortening the time required to acquire the image of the blood vessel and the time required to diagnose an abnormality of the blood vessel.

The effects obtained by the present disclosure are not limited to the aforementioned effects, and other effects, which are not mentioned above, will be clearly understood by those skilled in the art from the following description.

BRIEF DESCRIPTION OF THE DRAWINGS

Various aspects will be described with reference to the drawings, in which similar reference numerals are used to refer to similar components. In the following examples, for purposes of explanation, multiple specific details are set forth in order to provide a thorough understanding of one or more aspects. However, it will be apparent that such aspect(s) may be practiced without the specific details.

DETAILED DESCRIPTION

Figure 1:
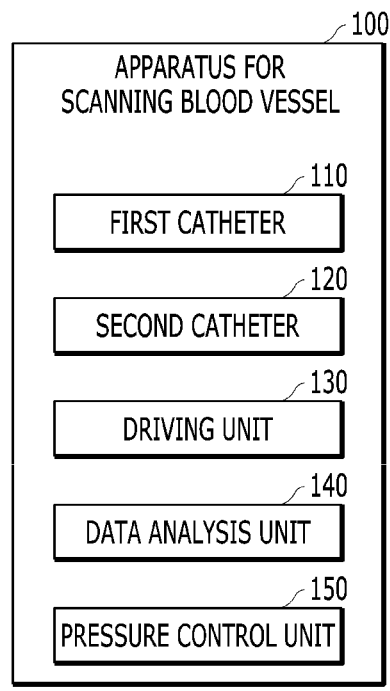
FIG. 1 is a block configuration view illustrating an apparatus for scanning a blood vessel according to several exemplary embodiments of the present disclosure.

Various exemplary embodiments and/or various aspects will be disclosed with reference to the drawings. In the following descriptions, for explanation, multiple specific details are disclosed in order to provide overall understandings of one or more aspects. However, it will also be appreciated by those skilled in the art that this aspect(s) may be practiced without these specific details. The following descriptions and the accompanying drawings are provided for disclosing specific exemplary aspects of the one or more aspects in detail. However, these aspects are exemplary. Thus, some of the various methods in the principles of the various aspects may be used, and the descriptions are intended to include all such aspects and their equivalents. Specifically, "embodiment", "example", "aspect", "exemplary embodiment" and the like used in this specification may not be construed as any aspect or design described being better or more advantageous than other aspects or designs.

Hereinafter, the same or similar constituent elements are assigned with the same reference numerals regardless of reference numerals, and the repetitive description thereof will be omitted. In addition, in the description of the exemplary embodiment disclosed in the present specification, the specific descriptions of publicly-known related technologies will be omitted when it is determined that the specific descriptions may obscure the subject matter of the exemplary embodiment disclosed in the present specification. In addition, the accompanying drawings are provided only to allow those skilled in the art to easily understand the exemplary embodiments disclosed in the present specification, and the technical spirit disclosed in the present specification is not limited by the accompanying drawings.

The terms used in the present specification are for explaining the exemplary embodiments, not for limiting the present disclosure. Unless particularly stated otherwise in the present specification, a singular form also includes a plural form. The term "comprise" and/or "comprising" used in the specification does not exclude existence or addition of one or more other constituent elements in addition to the mentioned constituent element.

Terms "first", "second", and the like may be used to describe various elements and components, but the elements and components are of course not limited by these terms. These terms are merely used to distinguish one element or component from another element or component. Therefore, the first element or component mentioned hereinafter may of course be the second element or component within the technical spirit of the present disclosure.

Unless otherwise defined, all terms (including technical and scientific terms) used in the present specification may be used as the meaning which may be commonly understood by the person with ordinary skill in the art, to which the present disclosure belongs. In addition, terms defined in a generally used dictionary shall not be construed in ideal or excessively formal meanings unless they are clearly and specially defined in the present specification.

The term "or" is intended to mean not an exclusive "or" but an inclusive "or". That is, unless specified or clear in context, "X uses A or B" is intended to mean one of the natural implicit substitutions. That is, "X uses A or B" can be applied to any of the cases where X uses A, X uses B, or X uses both A and B. Moreover, it is to be understood that the term "and/or" used in this specification refers to and includes all possible combinations of one or more of the listed related items.

The terms "information" and "data" used in the present specification may sometimes be interchangeably used.

When one constituent element is described as being "connected" or "coupled" to another constituent element, it should be understood that one constituent element can be connected or coupled directly to another constituent element, and an intervening constituent element can also be present between the constituent elements. When one constituent element is described as being "connected directly to" or "coupled directly to" another constituent element, it should be understood that no intervening constituent element is present between the constituent elements.

The suffixes "module" and "unit" used to describe some constituent elements in the following description are used together or interchangeably in order to facilitate the description in the specification, but the suffixes themselves do not have distinguishable meanings or functions.

When an element or layer is referred to as being "on" another element or layer, it can be directly on the other element or layer or intervening elements or layers may be present. In contrast, when an element is referred to as being "directly on" another element or layer, there are no intervening elements or layers present.

Spatially relative terms, such as "below," "beneath," "lower," "above," "upper," and the like, may be used herein for the ease of description of one constituent element or a correlation between one constituent element and other constituent elements, as illustrated in the drawings. It should be understood that the spatially relative terms encompass different orientations of the elements in use or operation in addition to the orientation depicted in the drawings.

For example, if the constituent element in the drawings is turned over, the constituent element described as "below" or "beneath" the other constituent element may then be placed "above" the other constituent element. Thus, the exemplary term "below" can encompass both orientations of above and below. The constituent elements may be oriented in different directions, and the spatially relative terms used herein may be interpreted in accordance with the orientations.

Objects and effects of the present disclosure and technical constituent elements for achieving the objects and effects will be clear with reference to the exemplary embodiments described in detail below together with the accompanying drawings. In addition, in the description of the present disclosure, the specific descriptions of publicly-known functions or configurations will be omitted when it is determined that the specific descriptions may unnecessarily obscure the subject matter of the present disclosure. In addition, the terms used herein are defined considering the functions in the present disclosure and may vary depending on the intention or usual practice of an inspector or an operator.

However, the present disclosure is not limited to the exemplary embodiments disclosed herein but will be implemented in various forms. The exemplary embodiments of the present disclosure are provided so that the present disclosure is completely disclosed, and a person with ordinary skill in the art can fully understand the scope of the present disclosure. The present disclosure will be defined only by the scope of the appended claims. Therefore, the definition of the present disclosure should be made based on the entire contents of the technology of the present specification.

The scope of the steps (methods) in the claims of the present disclosure is defined by the functions and features described in each of the steps but not affected by the order of description of each of the steps in the claims unless the precedence relationship of the sequence is specified in each of the steps. For example, in the claims described as including steps including step A and step B, even if step A is described before step B, the scope is not limited to the case in which step A should precede step B.

FIG. 1 is a block configuration view illustrating an apparatus for scanning a blood vessel according to several exemplary embodiments of the present disclosure.

Referring to FIG. 1, an apparatus 100 for scanning a blood vessel may include a first catheter 110, a second catheter 120, a driving unit 130, a data analysis unit 140, and a pressure control unit 150. However, the constituent elements illustrated in FIG. 1 is not essential to implement the apparatus 100 for scanning a blood vessel. The apparatus 100 for scanning a blood vessel, which is described in the present specification, may have the constituent elements larger or smaller in number than the constituent elements listed above.

Hereinafter, the first catheter 110 related to several exemplary embodiments of the present disclosure will be described.

According to the several exemplary embodiments of the present disclosure, the first catheter 110 may have an expandable balloon coated with a fluorescent material at a distal end thereof. In addition, the first catheter 110 may include a fluid transfer tube configured to transfer a fluid to the balloon so that the balloon is expanded.

In this case, the balloon may be formed in the form of an expandable and shrinkable balloon having an internal space that communicates with the fluid transfer tube included in the first catheter 110, and the balloon is provided at the distal end of the first catheter 110.

In the present disclosure, the fluid used to expand the balloon provided on the first catheter 110 may be a substance such as air or a physiological saline solution which is harmless to a human body even though the substance is introduced into organs. However, the present disclosure is not limited thereto.

Meanwhile, the first catheter 110 for applying the fluorescent material may be inserted into a blood vessel. Furthermore, the balloon provided on the first catheter 110 may be expanded at a target point in the blood vessel. In this case, the balloon may come into contact with an inner wall of the blood vessel at the target point in the blood vessel. In this case, the fluorescent material with which the balloon is coated may be applied to the inner wall of the blood vessel at the target point in the blood vessel.

In the present disclosure, the fluorescent material refers to a medicine administered so that specific tissue or blood vessels are clearly visible during imaging diagnosis.

Specifically, the fluorescent material may be applied to the target point in the blood vessel to increase contrast of the target point in the blood vessel so that a structure or lesion is observed. That is, the fluorescent material may mean a contrast agent, a fluorescent dye, or a fluorophore.

For example, the fluorescent material in the present disclosure may be indocyanine green (ICG). However, the present disclosure is not limited thereto, and the fluorescent material may be any material used to dye specific cells to diagnose intravascular lesion. Meanwhile, recently, 'compound designation green 16 (CDg16)', which is a fluorescent material used to selectively dye activated macrophages to diagnose arteriosclerosis, has been found.

In general, a near-infrared fluorescent image for diagnosing an abnormality of the blood vessel may be obtained after completely applying the fluorescent material (or the contrast agent) to the target point in the blood vessel.

According to a technology in the related art, several tens of minutes (20 minutes to 40 minutes) need to elapse until the fluorescent material is applied to the target point in the blood vessel after the fluorescent material is injected into the blood vessel by means of injection or the like.

In contrast, the first catheter 110 according to the several exemplary embodiments of the present disclosure applies the fluorescent material by bringing the fluorescent material into direct contact with the inner wall of the blood vessel at the target point in the blood vessel, and as a result, the fluorescent material may be immediately applied to the target point in the blood vessel.

Therefore, the first catheter 110 according to the several exemplary embodiments of the present disclosure may shorten the time required to elapse to apply the fluorescent material to the target point in the blood vessel.

A description of the first catheter 110 related to the first exemplary embodiment of the present disclosure will be described below in detail with reference to FIGS. 3 and 4.

Hereinafter, the first catheter 110 related to several other exemplary embodiments of the present disclosure will be described.

According to several other exemplary embodiments of the present disclosure, the first catheter 110 may have the balloon at the distal end thereof. In addition, the first catheter 110 may include the fluid transfer tube configured to transfer the fluid to the balloon so that the balloon is expanded. In addition, the first catheter 110 may include a fluorescent material transfer tube configured to transfer the fluorescent material.

The fluorescent material transfer tube included in the first catheter 110 may include a fluorescent material injection port provided at a proximal portion of the fluorescent material transfer tube and into which the fluorescent material is injected. In addition, the fluorescent material transfer tube may include at least one micro-hole provided at a distal portion. Furthermore, the fluorescent material may be discharged to the outside of the fluorescent material transfer tube through at least one micro-hole.

Meanwhile, the first catheter 110 for applying the fluorescent material may be inserted into the blood vessel. Furthermore, the balloon included in the first catheter 110 may be expanded to block one region of the blood vessel corresponding to the target point in the blood vessel. That is, the expanded balloon may block one side of the target point in the blood vessel to prevent the blood from flowing to the target point in the blood vessel.

When the balloon included in the first catheter 110 is expanded to block one region of the blood vessel corresponding to the target point in the blood vessel, the fluorescent material may be discharged to the outside of the fluorescent material transfer tube through at least one micro-hole. In this case, the fluorescent material discharged through the micro-hole may be applied to the target point in the blood vessel with the blocked one region thereof.

As described above, the near-infrared fluorescence image for diagnosing an abnormality of the blood vessel may be acquired after the fluorescent material (or the contrast agent) is completely applied to the target point in the blood vessel.

According to a technology in the related art, several tens of minutes (20 minutes to 40 minutes) need to elapse until the fluorescent material is applied to the target point in the blood vessel after the fluorescent material is injected into the blood vessel by means of injection or the like. In this case, one of the reasons why several tens of minutes are required to apply the fluorescent material is that the fluorescent material is mixed with the blood flowing along the blood vessel and concentration of the fluorescent material is decreased.

In contrast, the first catheter 110 according to the several exemplary embodiments of the present disclosure applies the fluorescent material by blocking one region of the blood vessel at the target point in the blood vessel and then discharging the fluorescent material, and as a result, it is possible to solve the problem in that the fluorescent material and the blood are mixed and the concentration of the fluorescent material is decreased.

The first catheter 110 according to the several exemplary embodiments of the present disclosure applies the fluorescent material to the target point in the blood vessel, and as a result, the time for which the fluorescent material moves in the blood vessel is not required.

That is, the first catheter 110 according to the several exemplary embodiments of the present disclosure maintains concentration of the fluorescent material and discharges (applies) the fluorescent material to the target point in the blood vessel or to a position adjacent to the target point, and as a result, it is possible to shorten the time required to elapse to apply the fluorescent material.

A description of the first catheter 110 related to the second exemplary embodiment of the present disclosure will be described below in detail with reference to FIGS. 5 to 10.

Hereinafter, the first catheter 110 related to several other exemplary embodiments of the present disclosure will be described.

According to several additional exemplary embodiments of the present disclosure, the first catheter 110 may have a plurality of balloons. In addition, the first catheter 110 may include the fluid transfer tube configured to transfer the fluid to the plurality of balloons so that the plurality of balloons is expanded. In this case, the fluid transfer tube is connected to the pressure control unit 150, such that the fluid discharged by the pressure control unit 150 may be transferred from the pressure control unit 150 to the plurality of balloons. However, the present disclosure is not limited thereto, and the pressure control unit 150 may draw the fluid, which has been transferred to the plurality of balloons, through the fluid transfer tube.

Specifically, the first catheter 110 may have a first balloon at the distal end thereof. Furthermore, the first catheter 110 may have a second balloon positioned at a position spaced apart from the distal end. That is, the first and second balloons included in the first catheter 110 may be positioned to be spaced apart from each other at a distance.

The first catheter 110 may include the fluorescent material transfer tube configured to transfer the fluorescent material.

The fluorescent material transfer tube included in the first catheter 110 may include the fluorescent material injection port provided at the proximal portion of the fluorescent material transfer tube and into which the fluorescent material is injected. In addition, the fluorescent material transfer tube may include at least one micro-hole provided at a distal portion.

Specifically, the fluorescent material transfer tube may have at least one micro-hole in a first region in a horizontal direction. Furthermore, the fluorescent material may be discharged to the outside of the fluorescent material transfer tube through at least one micro-hole.

The plurality of micro-holes from which the fluorescent material is discharged may be positioned between the first balloon and the second balloon. Specifically, the plurality of micro-holes may be included in the fluorescent material transfer tube positioned between the first balloon and the second balloon.

Meanwhile, the first catheter 110 for applying the fluorescent material may be inserted into the blood vessel. Furthermore, the first balloon and the second balloon included in the first catheter 110 may be expanded to block one region of the blood vessel corresponding to the target point in the blood vessel. That is, the expanded first and second balloons block both sides of the target point in the blood vessel, respectively, to prevent the blood from flowing to the target point in the blood vessel.

When the first balloon and the second balloon included in the first catheter 110 are expanded to block one region of the blood vessel corresponding to the target point in the blood vessel, the fluorescent material may be discharged to the outside of the fluorescent material transfer tube through at least one micro-hole. In this case, the fluorescent material discharged through the micro-hole may be applied to the target point in the blood vessel having the two blocked regions.

As described above, the near-infrared fluorescent image for diagnosing abnormality of the blood vessel may be acquired after the fluorescent material (or the contrast agent) is completely applied to the target point in the blood vessel.

According to a technology in the related art, several tens of minutes (20 minutes to 40 minutes) need to elapse until the fluorescent material is applied to the target point in the blood vessel after the fluorescent material is injected into the blood vessel by means of injection or the like. In this case, one of the reasons why several tens of minutes are required to apply the fluorescent material is that the fluorescent material is mixed with the blood flowing along the blood vessel and concentration of the fluorescent material is decreased.

In contrast, the first catheter 110 according to the several exemplary embodiments of the present disclosure applies the fluorescent material by blocking the two regions of the blood vessel at the target point in the blood vessel and then discharging the fluorescent material, and as a result, it is possible to solve the problem in that the fluorescent material and the blood are mixed and the concentration of the fluorescent material is decreased.

The first catheter 110 according to the several exemplary embodiments of the present disclosure applies the fluorescent material to the target point in the blood vessel, and as a result, the time for which the fluorescent material moves in the blood vessel is not required.

That is, the first catheter 110 according to the several exemplary embodiments of the present disclosure maintains concentration of the fluorescent material and discharges (applies) the fluorescent material to the target point in the blood vessel or to a position adjacent to the target point, and as a result, it is possible to shorten the time required to elapse to apply the fluorescent material.

Meanwhile, the fluorescent material may cause side effects to some subjects. In addition, if the fluorescent material is injected into the blood vessel of the subject having a side effect (e.g., an allergic reaction) to the fluorescent material, the fluorescent material is dispersed throughout the blood vessel, which may cause a fatal side effect to the subject's health.

In contrast, the first catheter 110 according to the several exemplary embodiments of the present disclosure locally applies the fluorescent material after blocking the two regions of the target point in the blood vessel, and as a result, it is possible to prevent a side effect fatal to the subject's health.

According to the several exemplary embodiments of the present disclosure, the fluid transfer tube and the fluorescent material transfer tube included in the first catheter 110 may be provided side by side.

According to several other exemplary embodiments of the present disclosure, the fluid transfer tube included in the first catheter 110 may be provided in the fluorescent material transfer tube. Specifically, the fluorescent material transfer tube surrounds the fluid transfer tube, and the plurality of micro-holes may be provided in an outer circumferential surface of the fluorescent material transfer tube.

The configuration in which the fluid transfer tube and the fluorescent material transfer tube included in the first catheter 110 are provided will be described below in detail with reference to FIGS. 6 and 8.

According to the several exemplary embodiments of the present disclosure, the second catheter 120 for scanning the blood vessel may be inserted into the blood vessel after the first catheter 110 is removed from the blood vessel. Furthermore, the second catheter 120 may include, at the distal end thereof, a scanning unit for acquiring scanning data.

Specifically, the second catheter 120 may scan the target point in the blood vessel which is coated with the fluorescent material. More specifically, the scanning unit of the second catheter 120 may acquire scanning data of the target point in the blood vessel. In this case, the scanning data may include data (e.g., data related to optical signals) for acquiring the near-infrared fluorescent image and the optical coherence tomography image.

Here, the second catheter 120 for acquiring the scanning data may be an OCT/NIRF (optical coherence tomography/near-infrared fluorescence) catheter.

Meanwhile, the data analysis unit 140 may acquire the microstructure information and the biochemical information of the blood vessel by using the optical signals acquired by the second catheter 120.

The microstructure information of the blood vessel may mean information about an external appearance of the blood vessel. The microstructure information of the blood vessel may include optical coherence tomography images.

The biochemical information of the blood vessel may mean information for diagnosing an abnormality of the blood vessel based on information on specific cells (e.g., macrophages) reacting with the fluorescent material (specifically, bonded to the fluorescent material). That is, the biochemical information of the blood vessel may mean information for diagnosing an abnormality of the blood vessel based on information about specific cells reacting with the fluorescent material.

For example, the macrophages, which react with the fluorescent material, are responsible for immunity of the body. Specifically, the macrophages are activated when the macrophages detect an invading substance in the body, and the macrophages produce antigens. That is, an inspector may check whether the blood vessel is abnormal by observing the macrophages that react with the fluorescent material.

Meanwhile, the biochemical information of the blood vessel may include near-infrared fluorescent images.

The second catheter 120 may acquire scanning data for producing the near-infrared fluorescent image and the intravascular ultrasonic image at the target point in the blood vessel. Here, the second catheter 120 may be an IVUS/NIRF (intravascular ultrasound/near-infrared fluorescence) catheter. In this case, the microstructure information of the blood vessel may include intravascular ultrasonic images.

However, the present disclosure is not limited thereto, and the second catheter 120 may acquire scanning data for producing near-infrared fluorescent images, optical coherence tomography images, and intravascular ultrasonic images. In this case, with the use of the scanning data, the data analysis unit 140 may acquire the microstructure information and the biochemical information of the blood vessel, that is, near-infrared fluorescent images, optical coherence tomography images, and intravascular ultrasonic images.

According to the several exemplary embodiments of the present disclosure, the driving unit 130 may include a rotary stage configured to rotate the catheter (each of the first catheter 110 and the second catheter 120) by 360 degrees, a connecting means configured to connect the rotary stage and the catheter, and a 1D motorized stage configured to move the catheter step by step.

The driving unit 130 may be connected to the first catheter 110 and the second catheter 120. Specifically, the driving unit 130 may be connected to the proximal end of the first catheter 110 when the first catheter 110 is inserted into the blood vessel. That is, the balloon is provided at the distal end of the first catheter 110, and the proximal end of the first catheter 110 may be connected to the driving unit 130.

Meanwhile, the driving unit 130 may be connected to the proximal end of the second catheter 120 when the second catheter 120 is inserted into the blood vessel. That is, the scanning unit for acquiring the scanning data is provided at the distal end of the second catheter 120, and the proximal end of the second catheter 120 may be connected to the driving unit 130.

The driving unit 130 may rotate and move the first catheter 110 and the second catheter 120 in the blood vessel. Specifically, the driving unit 130 may rotate and move the first catheter 110 and the second catheter 120 in the blood vessel so that the distal end of the first catheter 110 and the distal end of the second catheter 120 reach the target point in the blood vessel.

Figure 2:
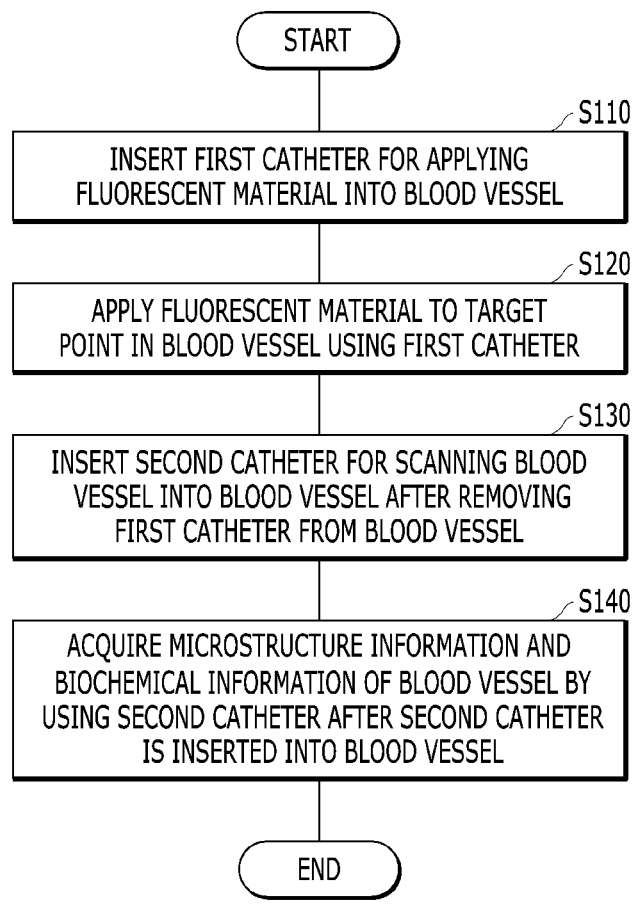
FIG. 2 is a flowchart for explaining an example of a method of scanning a blood vessel according to the several exemplary embodiments of the present disclosure.

FIG. 2 is a flowchart for explaining an example of a method of scanning a blood vessel according to the several exemplary embodiments of the present disclosure.

Referring to FIG. 2, the first catheter 110 for applying the fluorescent material to the blood vessel of the subject may be inserted into the blood vessel (S110). In this case, the fluorescent material to be applied to the blood vessel of the subject may be a material applied to scan the blood vessel of the subject (specifically, to acquire the near-infrared fluorescence image).

After step S110, the first catheter 110 may apply the fluorescent material to the target point in the blood vessel of the subject (S120). That is, the inspector may apply the fluorescent material to the target point in the blood vessel of the subject by using the first catheter 110.

According to the several exemplary embodiments of the present disclosure, the first catheter 110 having the expandable balloon coated with the fluorescent material at the distal end may apply the fluorescent material to the target point in the blood vessel of the subject.

Specifically, the balloon provided on the first catheter 110 may be expanded when the distal end of the first catheter 110 reaches the target point in the blood vessel of the subject.

More specifically, the pressure control unit 150 may expand the balloon by discharging the fluid when the balloon provided on the first catheter 110 reaches the target point in the blood vessel of the subject. In this case, the fluid discharged by the pressure control unit 150 may be transferred to the balloon through the fluid transfer tube from the pressure control unit 150. Therefore, the balloon may be expanded at the target point in the blood vessel of the subject.

In this case, the inner wall of the blood vessel at the target point in the blood vessel of the subject may come into contact with the expanded balloon. That is, the balloon coated with the fluorescent material comes into contact with the inner wall of the blood vessel at the target point in the blood vessel of the subject, such that the fluorescent material may be applied to the target point in the blood vessel.

Therefore, the inspector applies the fluorescent material by bringing the fluorescent material into direct contact with the inner wall of the blood vessel at the target point in the blood vessel of the subject, and as a result, it is possible to quickly apply the fluorescent material to the target point.

According to several other exemplary embodiments of the present disclosure, the first catheter 110, which has the expandable balloon at the distal end thereof and includes the fluorescent material transfer tube for applying the fluorescent material, may apply the fluorescent material to the target point in the blood vessel of the subject.

Specifically, the balloon provided on the first catheter 110 may be expanded when the distal end of the first catheter 110 reaches the target point in the blood vessel of the subject.

More specifically, the pressure control unit 150 may expand the balloon by discharging the fluid when the balloon provided on the first catheter 110 reaches the target point in the blood vessel of the subject. In this case, the fluid discharged by the pressure control unit 150 may be transferred to the balloon through the fluid transfer tube from the pressure control unit 150. Therefore, the balloon may be expanded at the target point in the blood vessel of the subject.

In this case, one region of the blood vessel corresponding to the target point in the blood vessel of the subject may be blocked.

After one region of the blood vessel corresponding to the target point in the blood vessel of the subject is blocked, the fluorescent material may be injected into the fluorescent material injection port provided at the proximal portion of the fluorescent material transfer tube. That is, the inspector may inject the fluorescent material into the fluorescent material injection port provided at the proximal portion of the fluorescent material transfer tube after one region of the blood vessel corresponding to the target point in the blood vessel of the subject is blocked.

In this case, the fluorescent material transfer tube may transfer the fluorescent material, which is injected into the fluorescent material injection port, to at least one micro-hole provided in the first region in the horizontal direction of the distal portion. In addition, the fluorescent material transfer tube may discharge the fluorescent material to the outside of the fluorescent material transfer tube through at least one micro-hole.

Therefore, the inspector applies the fluorescent material by discharging the fluorescent material after blocking one region of the blood vessel at the target point in the blood vessel of the subject, and as a result, it is possible to prevent the fluorescent material and the blood from being mixed, thereby preventing the time required to apply the fluorescent material from increasing.

According to several additional exemplary embodiments of the present disclosure, the first catheter 110, which has the plurality of expandable balloons and includes the fluorescent material transfer tube for applying the fluorescent material, may apply the fluorescent material to the target point in the blood vessel of the subject. In this case, the plurality of balloons may include the first balloon and the second balloon. Specifically, the plurality of balloons may include the first balloon provided at the distal end of the first catheter 110, and the second balloon positioned to be spaced apart from the distal end of the first catheter 110 at a distance.

Meanwhile, the first balloon and the second balloon provided on the first catheter 110 may be expanded when the distal end of the first catheter 110 reaches the region corresponding to the target point in the blood vessel of the subject.

Specifically, the pressure control unit 150 may discharge the fluid to expand the first balloon and the second balloon when the portion between the first balloon and the second balloon provided on the first catheter 110 is positioned in the region corresponding to the target point in the blood vessel of the subject. In this case, the fluid discharged by the pressure control unit 150 may be transferred to the first balloon and the second balloon through the fluid transfer tube from the pressure control unit 150.

In this case, the two regions of the blood vessel corresponding to the target point in the blood vessel of the subject may be blocked.

After one region of the blood vessel corresponding to the target point in the blood vessel of the subject is blocked, the fluorescent material may be injected into the fluorescent material injection port provided at the proximal portion of the fluorescent material transfer tube. That is, the inspector may inject the fluorescent material into the fluorescent material injection port provided at the proximal portion of the fluorescent material transfer tube after the two regions of the blood vessel corresponding to the target point in the blood vessel of the subject are blocked.

In this case, the fluorescent material transfer tube may transfer the fluorescent material, which is injected into the fluorescent material injection port, to at least one micro-hole positioned between the first balloon and the second balloon and provided in the first region in the horizontal direction. In addition, the fluorescent material transfer tube may discharge the fluorescent material to the outside of the fluorescent material transfer tube through at least one micro-hole.

Therefore, the inspector applies the fluorescent material by discharging the fluorescent material after blocking the two regions of the blood vessel at the target point in the blood vessel of the subject, and as a result, it is possible to prevent the fluorescent material and the blood from being mixed, thereby preventing the time required to apply the fluorescent material from increasing.

Meanwhile, the first catheter 110 may be removed (extracted) from the blood vessel of the subject after the fluorescent material is completely applied to the target point in the blood vessel of the subject. That is, the inspector may remove the first catheter 110 from the blood vessel of the subject after the fluorescent material is completely applied to the target point in the blood vessel.

After the first catheter 110 is removed from the blood vessel, the second catheter 120 for scanning the blood vessel may be inserted into the blood vessel from which the first catheter 110 is removed (S130). That is, the inspector may insert the second catheter 120 for scanning the blood vessel into the blood vessel after removing the first catheter 110.

After step S130, the microstructure information and the biochemical information of the blood vessel may be acquired by the second catheter 120 (S140). That is, the inspector may acquire the microstructure information and the biochemical information of the blood vessel by using the second catheter 120.

Specifically, the second catheter 120 may acquire the scanning data of the target point in the blood vessel. In this case, the scanning data may mean optical signals related to the optical coherence tomography image and the near-infrared fluorescence image. However, the present disclosure is not limited thereto.

As described above with reference to FIG. 1, the microstructure information of the blood vessel may include the optical coherence tomography image. That is, the microstructure information of the blood vessel may mean information about an external appearance of the blood vessel.

The biochemical information of the blood vessel may include near-infrared fluorescent images. That is, the biochemical information of the blood vessel may mean information for diagnosing an abnormality of the blood vessel based on information on specific cells (e.g., macrophages) reacting with the fluorescent material (specifically, bonded to the fluorescent material).

Therefore, the inspector may accurately check the state in the blood vessel of the subject based on the microstructure information related to the external appearance of the blood vessel of the subject and the biochemical information related to whether the blood vessel is abnormal.

The order of the above-mentioned steps in FIG. 2 may be changed as necessary, and at least one or more steps may be omitted or added. In addition, the above-mentioned steps are only examples of the present disclosure, and the scope of the present disclosure is not limited thereto.

Figure 3:
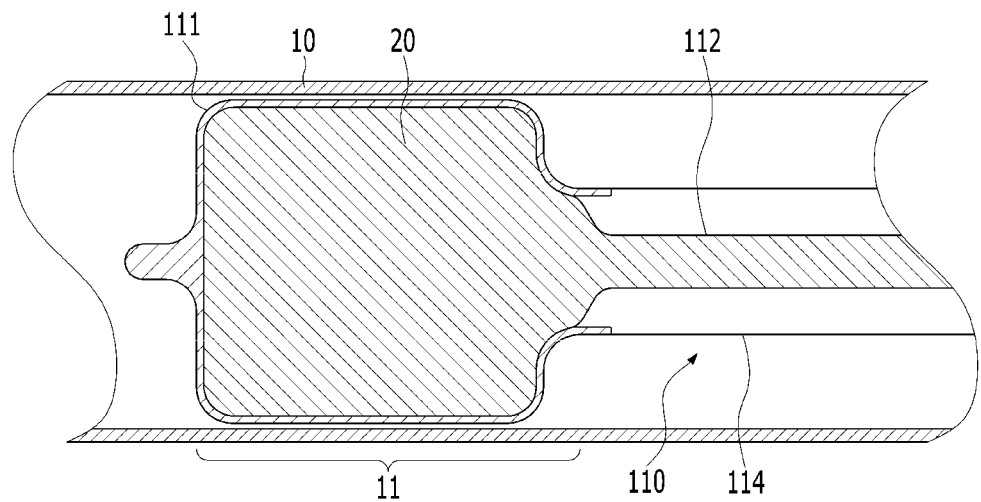
FIG. 3 is a view for explaining a first catheter according to the several exemplary embodiments of the present disclosure.

FIG. 3 is a view for explaining the first catheter according to the several exemplary embodiments of the present disclosure.

Referring to FIG. 3, the first catheter 110 may include a balloon 111, a fluid transfer tube 112, and an outer sheath 114.

As illustrated in FIG. 3, the balloon 111 may be provided at the distal end of the first catheter 110. In addition, the balloon 111 may have an internal space that communicates with the fluid transfer tube 112 included in the first catheter 110. In addition, the balloon 111 may be formed in the form of an expandable and shrinkable balloon.

An outer surface (i.e., a surface to be in contact with the inner wall of the blood vessel of the subject) of the balloon 111 may be coated with the fluorescent material. Specifically, one region of the outer sheath 114 surrounding the balloon 111 may be coated with the fluorescent material.

Meanwhile, when the balloon 111 is expanded at a target point 11 in a blood vessel 10 of the subject, the outer surface of the balloon 111 (i.e., one region of the outer sheath 114 surrounding the balloon 111) may come into contact with the target point 11 in the blood vessel 10 of the subject.

Therefore, the balloon 111 having the outer surface coated with the fluorescent material may apply the fluorescent material to the target point 11 in the blood vessel 10 of the subject.

The first catheter 110 according to the several exemplary embodiments of the present disclosure applies the fluorescent material by bringing the fluorescent material into contact with the target point 11 in the blood vessel 10 of the subject, and as a result, it is possible to save the time required to apply the fluorescent material.

The first catheter 110 immediately applies the fluorescent material to the target point 11 in the blood vessel 10, thereby enabling the second catheter 120 to quickly acquire the near-infrared fluorescent image together with the optical coherence tomography image.

Meanwhile, as described above, the fluid transfer tube 112 may communicate with the balloon 111. In addition, the fluid transfer tube 112 is connected to the pressure control unit 150, such that a fluid 20 discharged by the pressure control unit 150 may be transferred from the pressure control unit 150 to the balloon 111. That is, the balloon may be connected to the distal end of the fluid transfer tube 112, and the pressure control unit 150 may be connected to the proximal end of the fluid transfer tube 112. In this case, the fluid 20 may be a substance such as air or a physiological saline solution which is harmless to a human body even though the substance is introduced into body organs. However, the present disclosure is not limited thereto.

Meanwhile, a region of the first catheter 110, which is to be inserted into the blood vessel 10 of the subject, may be surrounded by the outer sheath 114. Specifically, the outer sheath 114 may be formed to surround the balloon 111 and the fluid transfer tube 112 of the first catheter 110.

Therefore, the outer sheath 114 may prevent the balloon 111 and the fluid transfer tube 112 from coming into direct contact with the blood vessel 10 of the subject. That is, the outer sheath 114 may prevent infection caused by a blood vessel insertion tool (in this case, the balloon 111 and the fluid transfer tube 112).

FIG. 4 is a view for explaining an example of a method applying the fluorescent material to the target point in the blood vessel by the first catheter according to the several exemplary embodiments of the present disclosure. The contents identical to the contents described above with reference to FIGS. 1 to 3 will not be repeatedly described again with reference to FIG. 4, and the drawing for assisting in understanding the present disclosure will be briefly described.

Figure 4A:
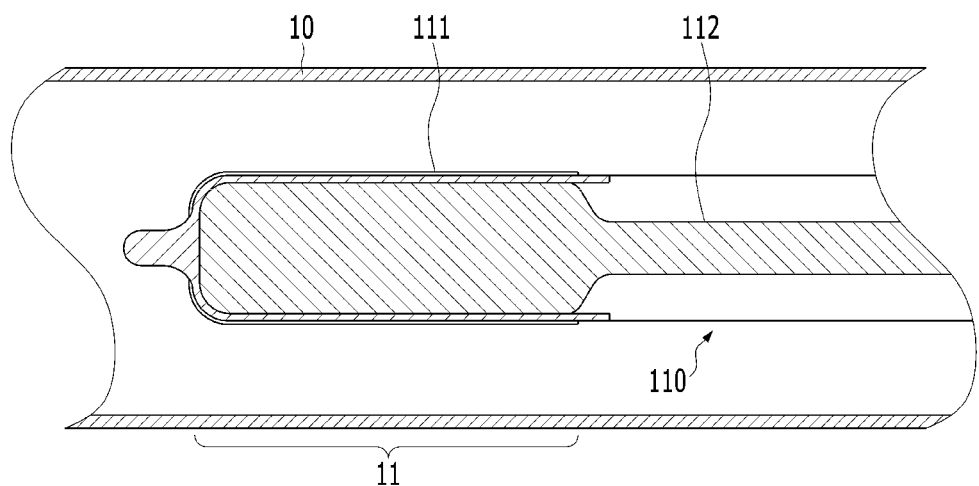
FIG. 4(a)-(b) is a view for explaining an example of a method applying a fluorescent material to a target point in a blood vessel by the first catheter according to the several exemplary embodiments of the present disclosure.

Referring to FIG. 4A, the first catheter 110 inserted into the blood vessel 10 of the subject may have the balloon 111 at the distal end. In this case, the balloon 111 may be coated with the fluorescent material.

Specifically, as illustrated, the balloon 111 of the first catheter 110 may be inserted into the blood vessel 10 of the subject in the state in which the balloon 111 is not expanded (i.e., the balloon is shrunk). That is, the balloon 111 illustrated in FIG. 4A may be in a state before the balloon 111 receives the fluid through the fluid transfer tube 112.

Figure 4B:
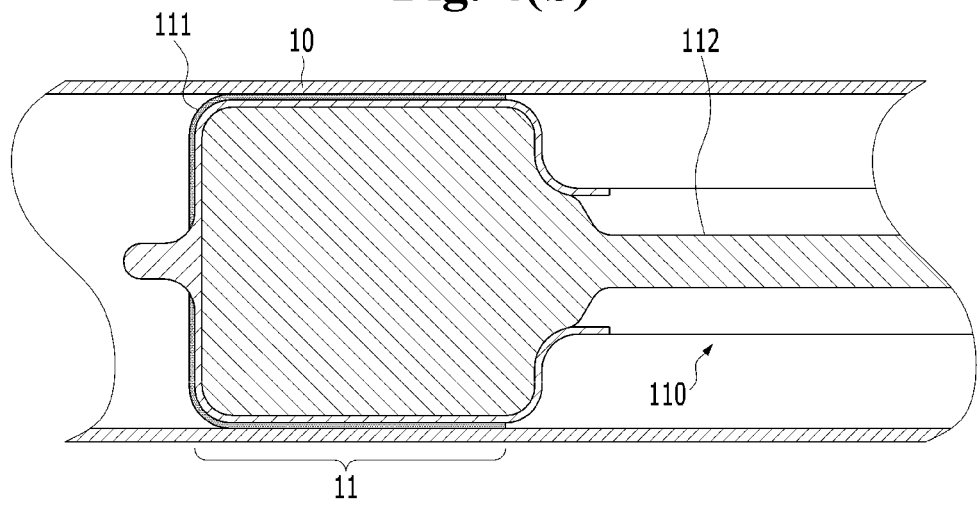

Referring to FIG. 4B, the balloon 111 of the first catheter 110 may be expanded at the target point 11 in the blood vessel 10 of the subject. In this case, the fluorescent material with which the balloon 111 is coated may be applied to the target point 11 in the blood vessel 10 of the subject.

That is, the first catheter 110 according to the several other exemplary embodiments of the present disclosure applies the fluorescent material by bringing the fluorescent material into direct contact with the inner wall of the blood vessel at the target point 11 in the blood vessel 10 of the subject, and as a result, the fluorescent material may be immediately applied to the target point 11 in the blood vessel 10 of the subject.

Therefore, the first catheter 110 according to the several exemplary embodiments of the present disclosure may shorten the time required to elapse to apply the fluorescent material to the target point 11 in the blood vessel 10 of the subject.

Figure 5:
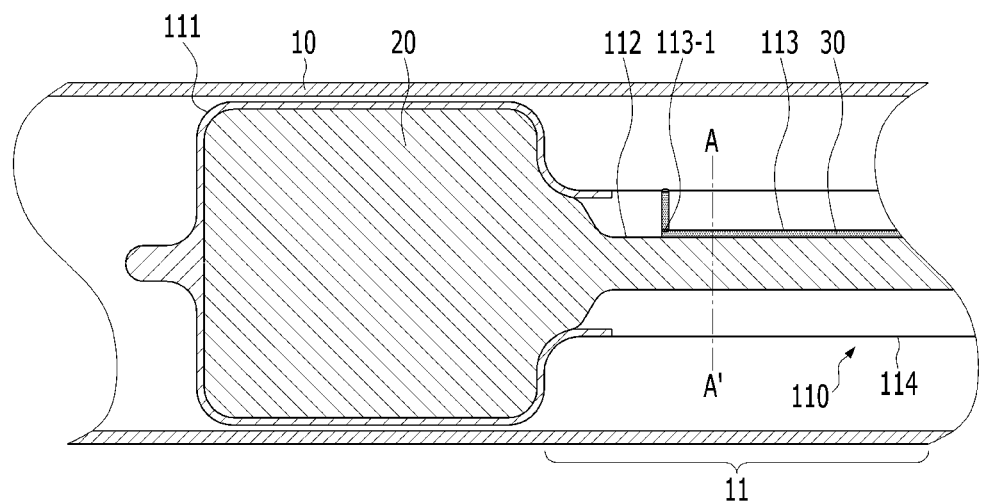
FIG. 5 is a view for explaining a first catheter according to several other exemplary embodiments of the present disclosure.

FIG. 5 is a view for explaining the first catheter according to several other exemplary embodiments of the present disclosure. FIG. 6 is a cross-sectional view of the first catheter illustrated in FIG. 5 taken along line A-A'.

Referring to FIG. 5, the first catheter 110 may include the balloon 111, the fluid transfer tube 112, at least one fluorescent material transfer tube 113, and the outer sheath 114.

As illustrated in FIG. 5, the first catheter 110 may have the balloon 111 at the distal end thereof. In this case, the balloon 111 may have the internal space that communicates with the fluid transfer tube 112 included in the first catheter 110. In addition, the balloon 111 may be formed in the form of an expandable and shrinkable balloon.

Meanwhile, the fluid transfer tube 112 is connected to the pressure control unit 150, such that a fluid 20 discharged by the pressure control unit 150 may be transferred from the pressure control unit 150 to the balloon 111. However, the present disclosure is not limited thereto, and the pressure control unit 150 may draw the fluid 20, which has been transferred to the balloon 111, through the fluid transfer tube 112. That is, the balloon 111 may be connected to the distal end of the fluid transfer tube 112, and the pressure control unit 150 may be connected to the proximal end of the fluid transfer tube 112.

At least one fluorescent material transfer tube 113 included in the first catheter 110 may include the fluorescent material injection port provided at the proximal portion of the at least one fluorescent material transfer tube 113 and into which a fluorescent material 30 is injected. In addition, the at least one fluorescent material transfer tube 113 may include at least one micro-hole 113-1 provided at the distal portion thereof.

Specifically, the at least one fluorescent material transfer tube 113 may have the at least one micro-hole 113-1 in the first region in the horizontal direction. Furthermore, the fluorescent material 30 may be discharged to the outside of the at least one fluorescent material transfer tube 113 through the at least one micro-hole 113-1.

More specifically, the at least one micro-hole 113-1 may discharge the fluorescent material 30 to the outside of the at least one fluorescent material transfer tube 113 through a tube that communicates with the outer sheath. That is, the fluorescent material may be discharged to the outside of the first catheter 110 through the at least one fluorescent material transfer tube 113, the at least one micro-hole 113-1, and the tube communicating with the outer sheath, and applied to the target point 11 in the blood vessel 10 of the subject.

According to the several exemplary embodiments of the present disclosure, the fluid transfer tube 112 and the at least one fluorescent material transfer tube 113 included in the first catheter 110 may be provided side by side.

Figure 6:
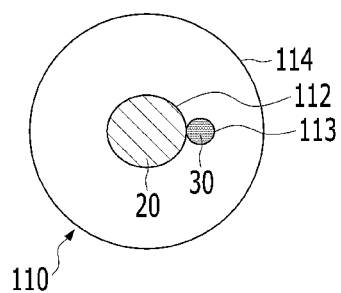
FIG. 6 is a cross-sectional view of the first catheter illustrated in FIG. 5 taken along line A-A'.

Referring to FIG. 6, the fluid transfer tube 112 and the at least one fluorescent material transfer tube 113 may be positioned in the region in the outer sheath 114 of the first catheter 110.

As illustrated, the fluid transfer tube 112 may have an internal space in which the fluid 20 may move. Furthermore, the at least one fluorescent material transfer tube 113 may have an internal space in which the fluorescent material 30 may move.

Meanwhile, the fluid transfer tube 112 and the at least one fluorescent material transfer tube 113 may be provided side by side at the adjacent positions in the region in the outer sheath 114 of the first catheter 110. That is, as illustrated in FIG. 6, one surface of the fluid transfer tube 112 and one surface of the at least one fluorescent material transfer tube 113 may be in contact with each other.

For example, the fluid transfer tube 112 and the at least one fluorescent material transfer tube 113 may have a '8' shape formed by connecting surfaces of two tubes when viewed from one side.

However, the positions at which the fluid transfer tube 112 and the at least one fluorescent material transfer tube 113 are provided described above with reference to FIG. 6 are merely several exemplary embodiments for assisting in understanding the present disclosure, and the present disclosure is not limited thereto.

Referring back to FIG. 5, the region of the first catheter 110, which is to be inserted into the blood vessel 10 of the subject, may be surrounded by the outer sheath 114. Specifically, the outer sheath 114 may be formed to surround the balloon 111, the fluid transfer tube 112, and the at least one fluorescent material transfer tube 113 of the first catheter 110.

Therefore, the outer sheath 114 may prevent the balloon 111, the fluid transfer tube 112, and the at least one fluorescent material transfer tube 113 from coming into direct contact with the blood vessel 10 of the subject. That is, the outer sheath 114 may prevent infection caused by a blood vessel insertion tool (in this case, the balloon 111, the fluid transfer tube 112, and the at least one fluorescent material transfer tube 113).

Figure 7:
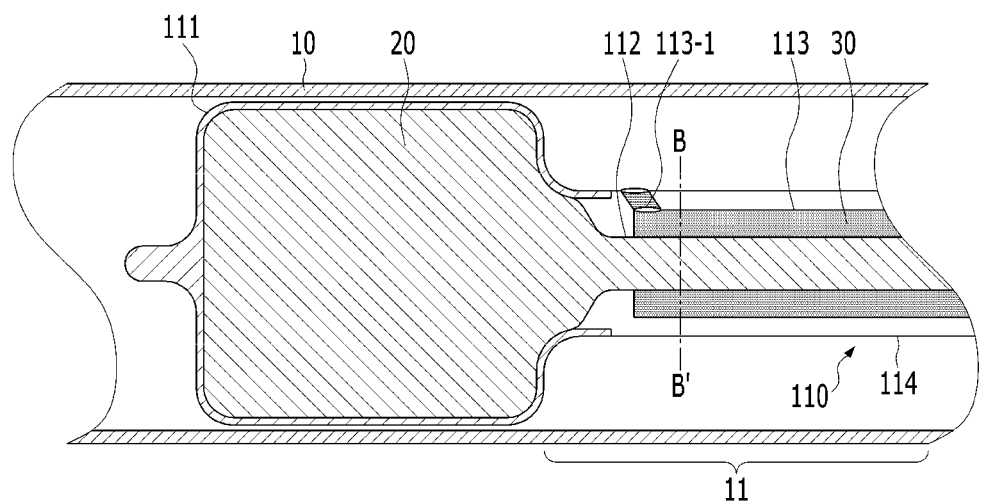
FIG. 7 is a view for explaining a first catheter according to several other exemplary embodiments of the present disclosure.

FIG. 7 is a view for explaining the first catheter according to several other exemplary embodiments of the present disclosure. FIG. 8 is a cross-sectional view of the first catheter illustrated in FIG. 7 taken along line B-B'.

Referring to FIG. 7, the first catheter 110 may include the balloon 111, the fluid transfer tube 112, the fluorescent material transfer tube 113, and the outer sheath 114.

As illustrated in FIG. 7, the first catheter 110 may have the balloon 111 at the distal end thereof. In this case, the balloon 111 may have the internal space that communicates with the fluid transfer tube 112 included in the first catheter 110. In addition, the balloon 111 may be formed in the form of an expandable and shrinkable balloon.

Meanwhile, the fluid transfer tube 112 is connected to the pressure control unit 150, such that a fluid 20 discharged by the pressure control unit 150 may be transferred from the pressure control unit 150 to the balloon 111. However, the present disclosure is not limited thereto, and the pressure control unit 150 may draw the fluid 20, which has been transferred to the balloon 111, through the fluid transfer tube 112. That is, the balloon 111 may be connected to the distal end of the fluid transfer tube 112, and the pressure control unit 150 may be connected to the proximal end of the fluid transfer tube 112.

The fluorescent material transfer tube 113 included in the first catheter 110 may include the fluorescent material injection port provided at the proximal portion of the fluorescent material transfer tube 113 and into which a fluorescent material 30 is injected. In addition, the fluorescent material transfer tube 113 may include at least one micro-hole 113-1 provided at the distal portion thereof.

Specifically, the fluorescent material transfer tube 113 may have the at least one micro-hole 113-1 in the first region in the horizontal direction. Furthermore, the fluorescent material 30 may be discharged to the outside of the fluorescent material transfer tube 113 through the at least one micro-hole 113-1.

More specifically, the at least one micro-hole 113-1 may discharge the fluorescent material 30 to the outside of the fluorescent material transfer tube 113 through a tube that communicates with the outer sheath. That is, the fluorescent material may be discharged to the outside of the first catheter 110 through the fluorescent material transfer tube 113, the at least one micro-hole 113-1, and the tube communicating with the outer sheath, and applied to the target point 11 in the blood vessel 10 of the subject.

According to the several exemplary embodiments of the present disclosure, the fluid transfer tube 112 included in the first catheter 110 may be provided in the fluorescent material transfer tube 113. Specifically, the fluorescent material transfer tube 113 surrounds the fluid transfer tube 112, and the plurality of micro-holes 113-1 may be provided in the outer circumferential surface of the fluorescent material transfer tube 113.

Figure 8:
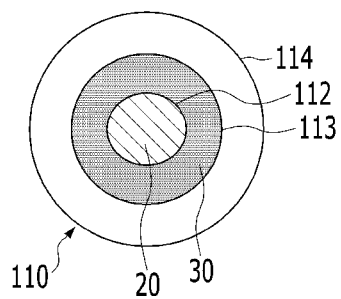
FIG. 8 is a cross-sectional view of the first catheter illustrated in FIG. 7 taken along line B-B'.

Referring to FIG. 8, the fluid transfer tube 112 and the fluorescent material transfer tube 113 may be positioned in the region in the outer sheath 114 of the first catheter 110.

As illustrated, the fluid transfer tube 112 may have the internal space in which the fluid 20 may move. Furthermore, the fluorescent material transfer tube 113 may have an internal space in which the fluorescent material 30 may move.

Meanwhile, the fluid transfer tube 112 may be provided to penetrate the internal space of the fluorescent material transfer tube 113. That is, as illustrated in FIG. 8, the fluid transfer tube 112 may be provided in one region of the internal space of the fluorescent material transfer tube 113.

Therefore, the fluid 20 may be transferred through the internal space of the fluid transfer tube 113 provided in one region of the internal space of the fluorescent material transfer tube 113. Furthermore, the fluorescent material 30 may be transferred through the region different from one region of the internal space of the fluorescent material transfer tube 113 in which the fluid transfer tube 112 is provided.

However, the positions at which the fluid transfer tube 112 and the fluorescent material transfer tube 113 are provided described above with reference to FIG. 8 are merely several exemplary embodiments for assisting in understanding the present disclosure, and the present disclosure is not limited thereto.

Referring back to FIG. 7, the region of the first catheter 110, which is to be inserted into the blood vessel 10 of the subject, may be surrounded by the outer sheath 114. Specifically, the outer sheath 114 may be formed to surround the balloon 111, the fluid transfer tube 112, and the fluorescent material transfer tube 113 of the first catheter 110.

Therefore, the outer sheath 114 may prevent the balloon 111, the fluid transfer tube 112, and the fluorescent material transfer tube 113 from coming into direct contact with the blood vessel 10 of the subject. That is, the outer sheath 114 may prevent infection caused by a blood vessel insertion tool (in this case, the balloon 111, the fluid transfer tube 112, the fluorescent material transfer tube 113).

FIG. 9 is a view for explaining an example of a method applying the fluorescent material to the target point in the blood vessel by the first catheter according to the several other exemplary embodiments of the present disclosure. The contents identical to the contents described above with reference to FIGS. 5 to 8 will not be repeatedly described again with reference to FIG. 9, and the drawing for assisting in understanding the present disclosure will be briefly described.

For the convenience of the description, the description in FIG. 9 will be described with reference to the basic drawings of the first catheter 110 described with reference to FIGS. 5 and 6. However, the contents illustrated in FIG. 9 are not limited thereto, and the same following exemplary embodiments may be applied to the first catheter 110 described with reference to FIGS. 7 and 8.

Figure 9A:
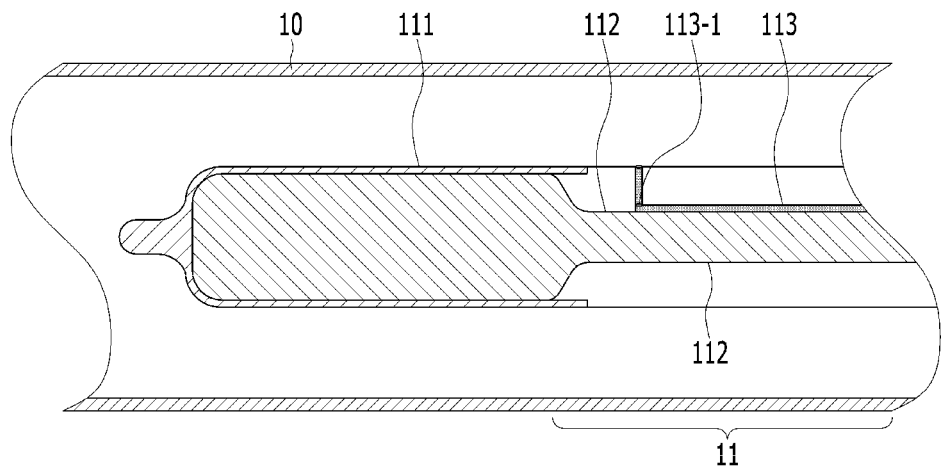
FIG. 9(a)-(c) is a view for explaining an example of a method applying a fluorescent material to a target point in a blood vessel by a first catheter according to the several other exemplary embodiments of the present disclosure.

Referring to FIG. 9A, the first catheter 110 inserted into the blood vessel 10 of the subject may have the balloon 111 at the distal end.

Specifically, as illustrated, the balloon 111 of the first catheter 110 may be inserted into the blood vessel 10 of the subject in the state in which the balloon 111 is not expanded (i.e., the balloon is shrunk). That is, the balloon 111 illustrated in FIG. 9A may be in a state before the balloon 111 receives the fluid through the fluid transfer tube 112.

Figure 9B:
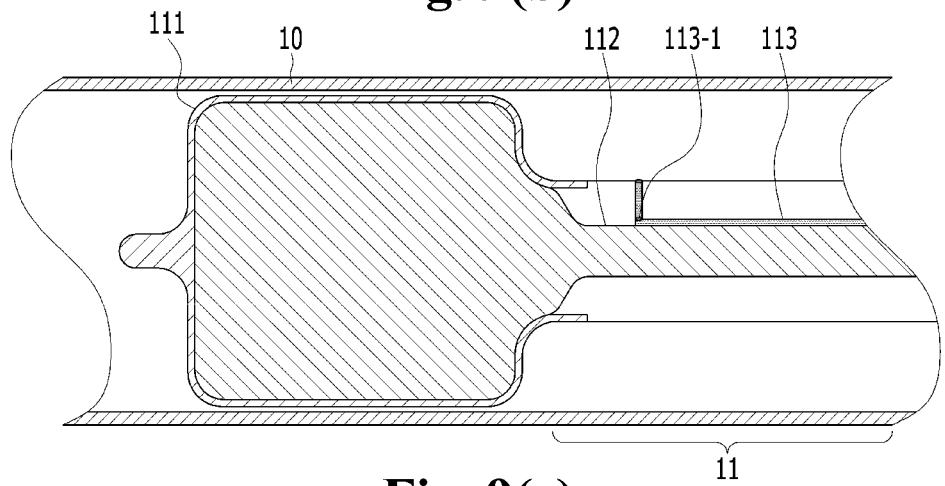

Referring to FIG. 9B, the balloon 111 of the first catheter 110 may be expanded at the target point 11 in the blood vessel 10 of the subject. In this case, one region of the target point 11 in the blood vessel 10 of the subject may be blocked by the balloon 111. That is, the expanded balloon 111 may block one side of the target point 11 in the blood vessel 10 of the subject to prevent the blood from flowing to the target point 11 in the blood vessel 10.

Figure 9C:
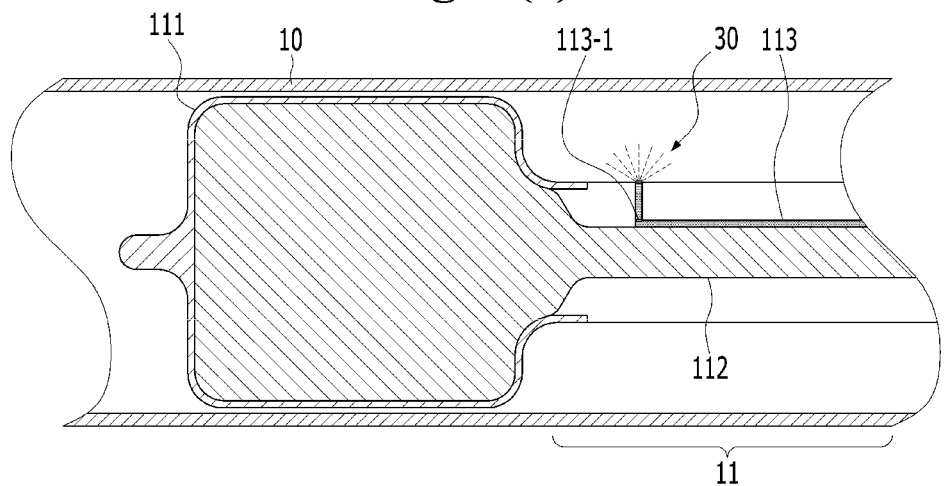

Referring to FIG. 9C, when the balloon 111 included in the first catheter 110 is expanded to block one region of the blood vessel corresponding to the target point 11 in the blood vessel 10, the fluorescent material 30 may be discharged to the outside of the fluorescent material transfer tube through the at least one micro-hole 113-1. In this case, the fluorescent material 30 discharged through the micro-hole 113-1 may be applied to the target point 11 in the blood vessel 10 having the blocked one region.

That is, the first catheter 110 according to the several exemplary embodiments of the present disclosure applies the fluorescent material by blocking one region of the blood vessel at the target point in the blood vessel and then discharging the fluorescent material, and as a result, it is possible to prevent the fluorescent material and the blood from being mixed, thereby preventing the time required to apply the fluorescent material from increasing. In addition, the first catheter 110 may minimize the time required to apply the fluorescent material, thereby enabling the second catheter 120 to quickly acquire the near-infrared fluorescent image together with the optical coherence tomography image.

Therefore, the first catheter 110 according to the several exemplary embodiments of the present disclosure may shorten the time required to elapse to apply the fluorescent material to the target point 11 in the blood vessel 10 of the subject.

Figure 10:
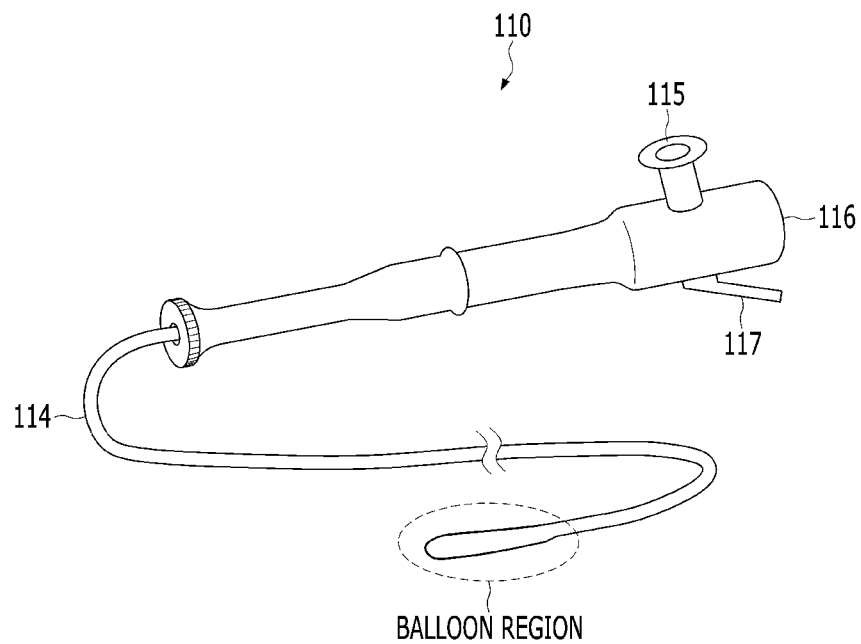
FIG. 10 is a view for explaining the first catheter according to the present disclosure.

FIG. 10 is a view for explaining the first catheter according to the present disclosure.

As described above, the first catheter 110 according to the several exemplary embodiments of the present disclosure may apply the fluorescent material to the target point in the blood vessel through the at least one micro-hole of the fluorescent material transfer tube after the balloon is expanded.

Referring to FIG. 10, the first catheter 110 may have the balloon in a balloon region positioned at the distal portion. Because the balloon region has been described in detail with reference to FIGS. 3 to 9, a specific description thereof will be omitted.

The first catheter 110 may have a fluorescent material injection port 115, a connector 116, and a latch 117 at the proximal portion thereof.

The fluorescent material injection port 115 may receive the fluorescent material after the balloon of the first catheter 110 is expanded. That is, the inspector may expand the balloon of the first catheter 110 and then inject the fluorescent material into the fluorescent material injection port 115.

In this case, the fluorescent material may be applied to the target point in the blood vessel of the subject through at least one micro-hole of the fluorescent material transfer tube.

Specifically, the fluorescent material injection port 115 may be connected to the proximal end of the fluorescent material transfer tube. That is, the fluorescent material may be injected into the fluorescent material injection port 115, may pass through the fluorescent material transfer tube, and then may be applied to the target point in the blood vessel through at least one micro-hole provided at the distal end of the fluorescent material transfer tube.

Meanwhile, the connector 116 may connect the first catheter 110 to the apparatus 100 for scanning a blood vessel.

Specifically, the first catheter 110 receives motion ability provided from the driving unit 130 through the connector 116 and may rotate and move in the blood vessel. In addition, the first catheter 110 may receive the fluid for expanding the balloon from the pressure control unit 150 of the apparatus 100 for scanning a blood vessel through the connector 116.

However, the present disclosure is not limited thereto, and the first catheter 110 may receive, through the connector 116, various motion abilities, control signals, and specific substances, which are required to operate the first catheter 110, from the apparatus 100 for scanning a blood vessel.

Meanwhile, a latch 117 provided on the proximal portion of the first catheter 110 may be used to disconnect the first catheter 110 connected to the apparatus 100 for scanning a blood vessel. That is, in order to disconnect the first catheter 110 connected to the apparatus 100 for scanning a blood vessel, the inspector may disconnect the first catheter 110 by pulling or pushing the latch 117 provided at the proximal portion of the first catheter 110.

Figure 11:
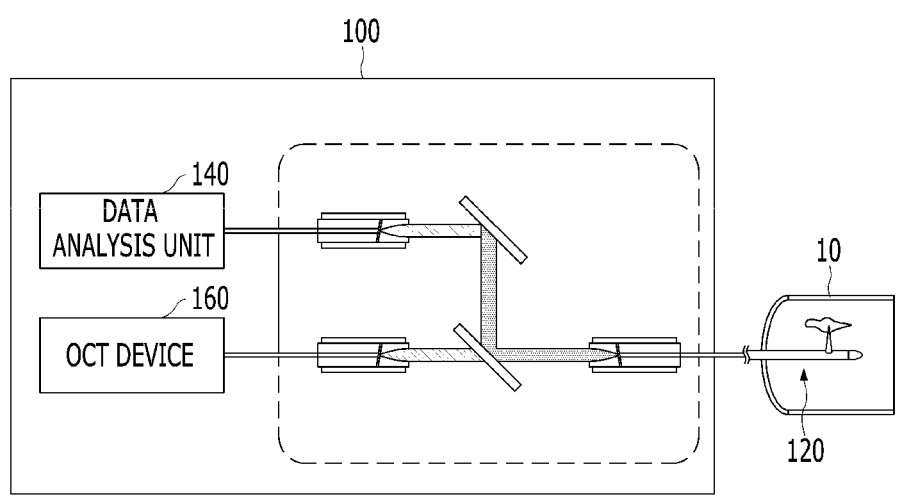
FIG. 11 is a view for explaining an example of a method of acquiring microstructure information and biochemical information of a blood vessel by a second catheter according to several exemplary embodiments of the present disclosure.

FIG. 11 is a view for explaining an example of a method of acquiring microstructure information and biochemical information of the blood vessel by a second catheter according to several exemplary embodiments of the present disclosure.

According to the several exemplary embodiments of the present disclosure, the second catheter 120 may acquire the scanning data of the target point in the blood vessel. In this case, the scanning data may include the optical signal for acquiring at least one of the optical coherence tomography image and the intravascular ultrasonic image.

Specifically, referring to FIG. 11, the second catheter 120 may be connected to the apparatus 100 for scanning a blood vessel in order to acquire the microstructure information and the biochemical information of the blood vessel. More specifically, the second catheter 120 may be connected to a data analysis unit 140 and an OCT device 160 of the apparatus 100 for scanning a blood vessel.

The OCT device 160 may transmit first light to the second catheter 120 by means of a first light source in order to acquire the optical coherence tomography image. In this case, the second catheter 120 may emit the first light to the target point in the blood vessel.

The OCT device 160 may transmit second light to the second catheter 120 by means of a second light source in order to acquire the near-infrared fluorescence image. In this case, the second catheter 120 may emit the second light to the target point in the blood vessel.

Meanwhile, the second catheter 120 may acquire the optical signal reflected at the target point in the blood vessel as the first light and the second light are emitted. Furthermore, the second catheter 120 may transmit the light, which is reflected at the target point in the blood vessel, to the data analysis unit 140. In this case, the data analysis unit 140 may acquire the optical coherence tomography image and the near-infrared fluorescent image by using the light reflected at the target point in the blood vessel. Here, the second catheter 120 may be an OCT/NIRF (optical coherence tomography/near-infrared fluorescence) catheter.

Therefore, the inspector may accurately check the state of the blood vessel of the subject based on the microstructure information related to the external appearance of the blood vessel of the subject and the biochemical information related to whether the blood vessel is abnormal.

The description of the presented exemplary embodiments is provided to enable any person skilled in the art of the present disclosure to carry out or use the present disclosure. Various modifications to the exemplary embodiments will be apparent to those skilled in the art of the present disclosure, and the generic principles defined herein may be applied to other exemplary embodiments without departing from the scope of the present disclosure. Accordingly, it should be understood that the present disclosure is not limited to the exemplary embodiments presented herein but should be construed in the broadest scope consistent with the principles and novel features presented herein.

MODE FOR INVENTION

As described above, the related contents have been described in the best mode for carrying out the invention.

INDUSTRIAL APPLICABILITY

The present disclosure relates to a method and an apparatus for scanning a blood vessel, and more particularly, to a method and an apparatus for scanning a blood vessel that acquire microstructure information and biochemical information of a blood vessel.

What is claimed is:

1. A method of scanning a blood vessel comprising:
   for applying a fluorescent material into the blood vessel, inserting a first catheter comprising a fluorescent material transfer tube having at least one micro-hole in a first region in a horizontal direction and transferring the fluorescent material to the at least one micro-hole so that the fluorescent material is discharged from the at least one micro-hole;
   applying the fluorescent material to a target point in the blood vessel using the first catheter;
   inserting a second catheter for scanning the blood vessel into the blood vessel after removing the first catheter from the blood vessel; and
   acquiring microstructure information and biochemical information of the blood vessel by using the second catheter after the second catheter is inserted into the blood vessel.

2. The method of claim 1, wherein the first catheter has an expandable balloon coated with the fluorescent material at a distal end.

3. The method of claim 2, wherein the applying of the fluorescent material to the target point in the blood vessel using the first catheter comprises:
   expanding the expandable balloon of the first catheter so that the expandable balloon contacts an inner wall of the blood vessel at the target point and the fluorescent material is applied to the inner wall of the blood vessel at the target point.

4. The method of claim 1, wherein the first catheter further comprises:
   a balloon; and
   a fluid transfer tube having the balloon at a distal end and transferring a fluid to the balloon so that the balloon is expandable.

5. The method of claim 4, wherein the applying of the fluorescent material to the target point in the blood vessel using the first catheter comprises:
   expanding the balloon to block a region of the blood vessel corresponding to the target point in the blood vessel; and
   discharging the fluorescent material to an outside of the fluorescent material transfer tube through the at least one micro hole when the balloon is expanded.

6. The method of claim 1, wherein the acquiring of the microstructure information and the biochemical information of the blood vessel by using the second catheter after the second catheter is inserted into the blood vessel comprises:
   acquiring an optical coherence tomography image together with a near-infrared fluorescence image of the target point using the second catheter.

7. Apparatus for scanning blood vessel comprising:
   a first catheter comprising a fluorescent material transfer tube having at least one micro-hole in a first region in a horizontal direction and transferring the fluorescent material to the at least one micro-hole so that the fluorescent material is discharged from the at least one micro-hole, for applying a fluorescent material to a target point in the blood vessel;
   a second catheter for scanning the target point in the blood vessel to which the fluorescent material is applied;
   a driving unit for rotating and moving the first catheter or the second catheter; and
   a data analysis unit that acquires microstructure information and biochemical information of the blood vessel based on scanning data scanned by the second catheter.

8. The apparatus of claim 7, wherein the first catheter has an expandable balloon coated with the fluorescent material at a distal end.

9. The apparatus of claim 8, further comprising:
   a pressure control unit coupled to a proximal end of the first catheter and injecting a fluid for expanding the expandable balloon into the expandable balloon so that the expandable balloon contacts an inner wall of the blood vessel at the target point so that the fluorescent material is applied to the inner wall of the blood vessel at the target point.

10. The apparatus of claim 7, wherein the first catheter comprises:
    a balloon; and
    a fluid transfer tube having the balloon at a distal end and transferring a fluid to the balloon so that the balloon is expandable.

11. The apparatus of claim 10, further comprising:
a pressure control unit coupled to a proximal end of the first catheter and injecting a fluid for expanding the balloon into the balloon for blocking a region of the blood vessel corresponding to the target point in the blood vessel; and
a fluorescent material injection port provided at proximal portion of the fluorescent material transfer tube and into which the fluorescent material is injected.

12. The apparatus of claim 7, wherein the microstructure information comprises optical coherence tomography images, and
wherein the biochemical information comprises near-infrared fluorescence images.

\* \* \* \* \*